US009766258B2

(12) United States Patent
Itoh

(10) Patent No.: US 9,766,258 B2
(45) Date of Patent: Sep. 19, 2017

(54) CARRYING APPARATUS

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 0 days.

(21) Appl. No.: 14/620,714

(22) Filed: Feb. 12, 2015

(65) Prior Publication Data

US 2015/0226760 A1 Aug. 13, 2015

(30) Foreign Application Priority Data

Feb. 12, 2014 (JP) ................................ 2014-024682

(51) Int. Cl.

*B65G 33/04* (2006.01)
*B65G 54/02* (2006.01)
*G01N 35/04* (2006.01)
*B65G 35/06* (2006.01)

(52) U.S. Cl.

CPC ............. *G01N 35/04* (2013.01); *B65G 33/04* (2013.01); *B65G 35/066* (2013.01); *B65G 54/02* (2013.01); *G01N 2035/0477* (2013.01); *G01N 2035/0487* (2013.01)

(58) Field of Classification Search

CPC ........ B65G 33/04; B65G 54/02; B65G 35/06; B65G 35/063; B65G 2201/02; G01N 35/04; G01N 2035/0477; G01N 2035/0487

See application file for complete search history.

(56) References Cited

U.S. PATENT DOCUMENTS 3,622,128 A 11/1971 Gelser
5,377,816 A 1/1995 Deligi et al.
5,881,649 A * 3/1999 Hasegawa ......... H01L 21/67709 104/166
5,906,262 A 5/1999 Miki
5,913,401 A 6/1999 Tamura et al.
6,251,232 B1 6/2001 Aruga et al.
6,471,469 B2 * 10/2002 Toffan .................. F01D 11/003 29/888.3

(Continued)

FOREIGN PATENT DOCUMENTS

CN 1513739 7/2004
CN 2905177 5/2007

(Continued)

OTHER PUBLICATIONS

Extended European Search Resort issued in Application No. 15000393.7 dated May 15, 2015.

(Continued)

*Primary Examiner* — Mark A Deuble
(74) *Attorney, Agent, or Firm* — Nixon & Vanderhye P.C.

(57) ABSTRACT

A carrying apparatus includes a holder which houses an object to be carried and which comprises a holder side member; a carrying path which guides the movement of the holder; a helical member which generates, between the holder side member and the helical member, a first force in a direction to depart from the holder side member or a second force to attract the holder side member and which is disposed along the carrying path; and a rotation unit which rotates the helical member.

1 Claim, 4 Drawing Sheets

F3 37 37 10 12 36 37 36 20 50 30 11 55 65 35 31 33 65 65 52 53 60 34 38 32 65 63 A 62 63 54 61 53a F3

(56) References Cited

U.S. PATENT DOCUMENTS

| | | | | |
|---|---|---|---|---|
| 6,561,343 | B2 * | 5/2003 | Miyauchi | B65G 54/02 198/619 |
| 7,207,241 | B2 | 4/2007 | Itoh | |
| 7,264,111 | B2 * | 9/2007 | Veiner | G01N 35/04 198/465.1 |
| 8,261,905 | B2 * | 9/2012 | Kholodenko | H01L 21/67706 198/467.1 |
| 9,027,739 | B2 * | 5/2015 | Hosek | F16D 3/00 198/619 |
| 2002/0060134 | A1 | 5/2002 | Miyauchi et al. | |
| 2005/0271555 | A1 | 12/2005 | Itoh | |
| 2006/0278497 | A1 | 12/2006 | White et al. | |
| 2009/0260457 | A1 | 10/2009 | Itoh | |
| 2010/0226828 | A1 * | 9/2010 | Itoh | B01L 9/06 422/562 |
| 2013/0233673 | A1 | 9/2013 | Itoh | |
| 2015/0226760 | A1 | 8/2015 | Itoh | |

FOREIGN PATENT DOCUMENTS

| | | | |
|---|---|---|---|
| CN | 103303639 | | 9/2013 |
| EP | 2 642 300 | A1 | 9/2013 |
| JP | 4-365666 | A | 12/1992 |
| JP | 4522463 | | 6/2010 |
| KR | 10-2013-0103408 | | 9/2013 |
| TW | M444363 | | 1/2013 |

OTHER PUBLICATIONS

Extended European Search Report issued in Application No. 15000393.7 dated May 21, 2015.

Canadian Office Action issued in Application No. 2,882,013 dated Dec. 14, 2015.

Chinese Office Action issued in Application No. 201510073954.X dated Jan. 12, 2016 (w/ translation).

Taiwanese Office Action issued Application No. 104104740 dated Jan. 8, 2016 (w/ translation).

Korean Office Action issued in App. No. 10-2015-0021117 dated Feb. 26, 2016 (w/ translation).

European Office Action issued in App. No. 15 000 393.7 dated Jun. 17, 2016.

Chinese Office Action issued in App. No. 201510073954.X dated Sep. 29, 2016.

Extended European Search issued in App. No. 16162361.6 dated Aug. 4, 2016.

U.S. Office Action dated U.S. Appl. No. 15/083,514, filed Sep. 29, 2016.

Canadian Office Action issued in App. No. 2,882,013 dated Nov. 1, 2016.

Taiwanese Office Action issued in App. No. 105109514 dated Feb. 21, 2017 (w/ translation).

U.S. Office Action issued in U.S. Appl. No. 15/083,514 dated Mar. 10, 2017.

Taiwanese Office Action issued in App. No. 105109514 dated Nov. 24, 2016 (w/ translation).

Chinese Office Action issued in App. No. 201510073954.X dated Jan. 13, 2017 (w/ translation).

Canadian Office Action issued in App. No. 2,924,896 dated Feb. 20, 2017.

Chinese Office Action issued in Appln. No. 201510073954.X dated Apr. 26, 2017 (w/ translation).

* cited by examiner

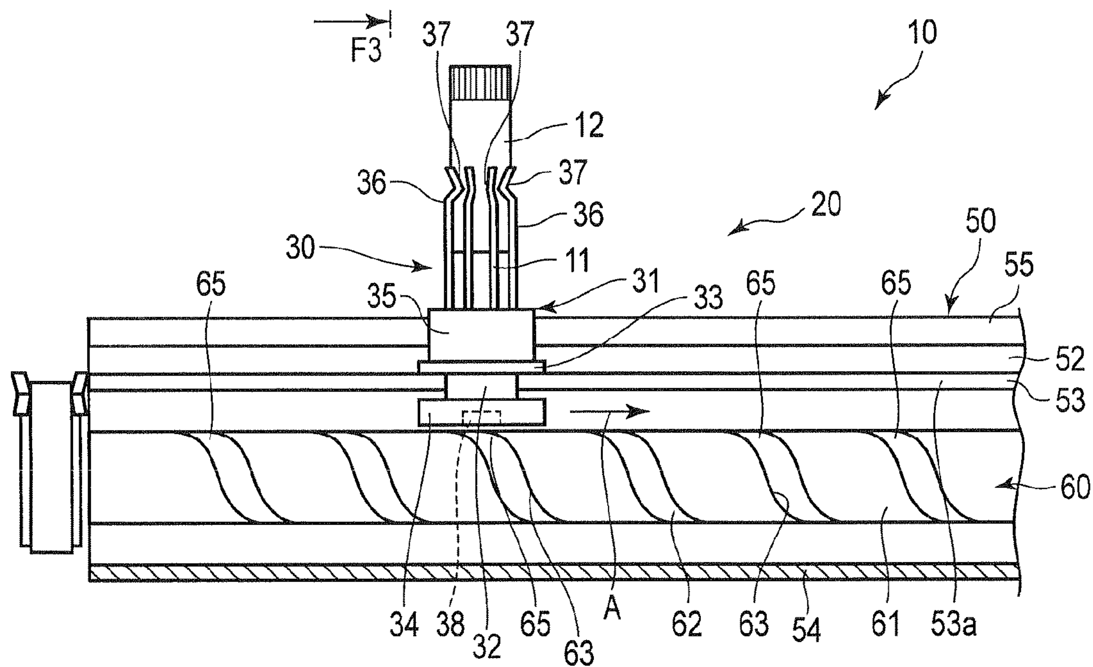
F I G. 2
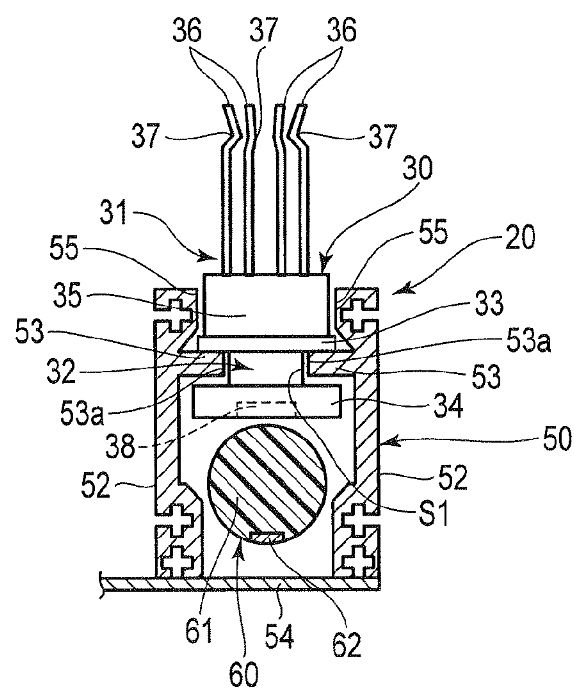
F I G. 3

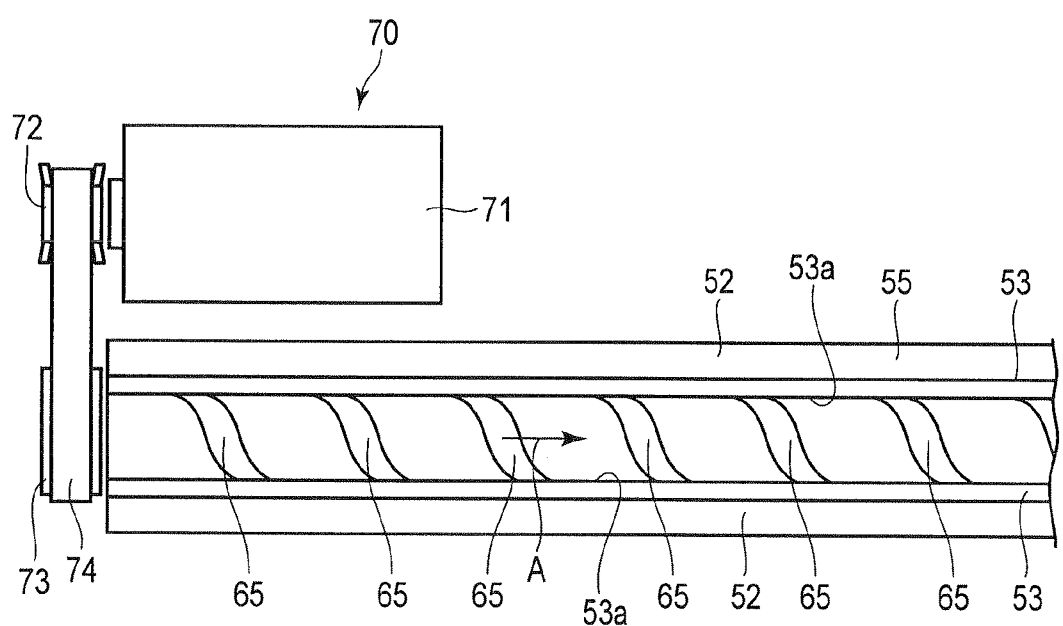
F I G. 4

CARRYING APPARATUS

CROSS-REFERENCE TO RELATED APPLICATIONS

This application is based upon and claims the benefit of priority from prior Japanese Patent Application No. 2014-24682, filed Feb. 12, 2014, the entire contents of which are incorporated herein by reference.

BACKGROUND OF THE INVENTION

Field of the Invention

The present invention relates to a carrying apparatus which carries a sample such as blood.

Description of the Related Art

A sample processing system which processes a sample such as blood has been suggested. The sample processing system of this type has a processing apparatus which processes the sample, and a carrying apparatus which carries the sample to the processing apparatus. The carrying apparatus has a sample holder which holds the sample, and a carrying path to carry the sample holder to the processing apparatus. The sample is housed in a container such as a test tube. The sample holder removably holds the test tube.

A structure that uses a carrying belt has been suggested as the structure of the carrying path. A carrying path of this type has a belt to mount the sample holder, and a belt driver which drives the carrying belt.

The carrying belt is an endless belt which is formed into a ring shape by way of example. The belt driver rotates to move on the carrying belt in its circumferential direction. If the carrying belt is rotated, the sample holder moves in response to the movement of the carrying belt. As a result, the sample holder is carried. A carrying apparatus of this type has been disclosed in, for example, Japanese Patent No. 4522463.

The above-mentioned carrying apparatus has the following problems: In the sample processing apparatus, multiple sample holders are generally mounted on one carrying belt to process multiple sample holders. Therefore, when a predetermined sample holder is stopped at a predetermined position on the carrying path, the driving of the carrying belt is not stopped, but a stopper, for example, is used to stop the predetermined sample holder alone at the predetermined position. The sample holder is held by the stopper to stop the movement of the sample holder. In this case, the carrying belt is driven to carry other samples.

Thus, friction is generated between the carrying belt and the sample holder which is stopped by the stopper. The carrying belt is worn by this friction. If the carrying belt is further worn, the carrying belt will be replaced. A higher replacement frequency of the carrying belt increases costs.

BRIEF SUMMARY OF THE INVENTION

According to an aspect of embodiments, a carrying apparatus includes a holder which houses an object to be carried and which comprises a holder side member; a carrying path which guides the movement of the holder; a helical member which generates, between the holder side member and the helical member, a first force in a direction to depart from the holder side member or a second force to attract the holder side member and which is disposed along the carrying path; and a rotation unit which rotates the helical member.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view of the sample processing system taken along the line F2-F2 indicated in FIG. 1;

FIG. 3 is a sectional view of the sample processing system taken along the line F3-F3 indicated in FIG. 2;

FIG. 4 is a plan view showing one end of a carrying path of the carrying apparatus in a longitudinal direction.

DETAILED DESCRIPTION OF THE INVENTION

Figure 1:
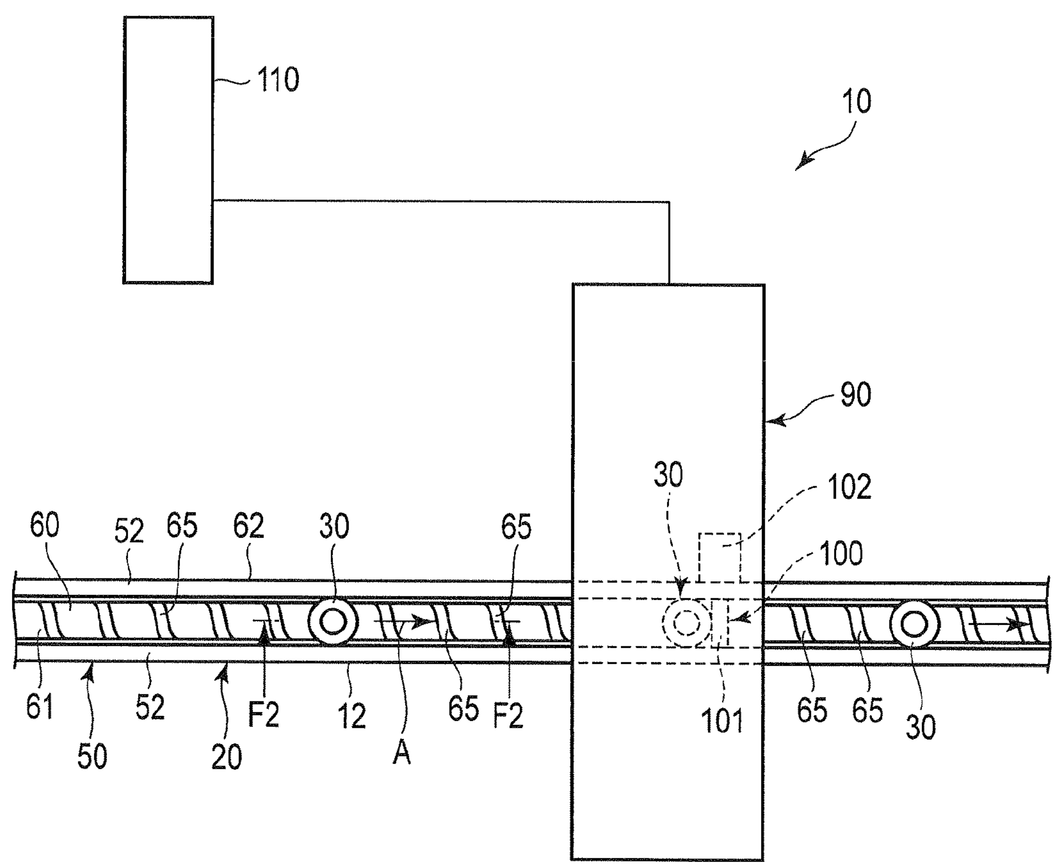
FIG. 1 is a plan view showing part of a sample processing system having a carrying apparatus according to one embodiment of the present invention.

A carrying apparatus according to one embodiment of the present invention will be described with reference to FIG. 1 to FIG. 5. FIG. 1 is a plan view showing part of a sample processing system 10 having a carrying apparatus 20 according to the present embodiment. As shown in FIG. 1, the sample processing system 10 has the carrying apparatus 20 which carries a later-described sample holder 30, a processing apparatus 90 which processes a sample 11 held by the sample holder 30, a stopper apparatus 100 which selectively stops the sample holder 30 on a carrying path 50 of the carrying apparatus 20, and a controller 110 which controls the operations of the carrying apparatus 20 and the processing apparatus 90.

FIG. 2 is a sectional view of the sample processing system 10 taken along the line F2-F2 indicated in FIG. 1. FIG. 2 shows how the sample holder 30 is placed on the lacer-described carrying path 50 along the extending direction of the carrying path 50. In FIG. 2, the sample holder 30 is not cut.

As shown in FIG. 2, the sample 11 is, for example, blood, and is housed in, for example, a test tube 12. The test tube 12 is an example of an object to be carried. The processing apparatus 90 processes the sample 11. The processing is, for example, dispensing. The processing performed by the processing apparatus is not exclusively the dispensing. A processing apparatus which not only performs the processing for the sample 11 but also the processing necessary for the test tube 12 may be provided. FIG. 1 shows the part of the sample processing system 10 in the vicinity of the processing apparatus 90.

FIG. 3 is a sectional view of the sample processing system 10 taken along the line F3-F3 indicated in FIG. 2. FIG. 3 shows the front of the sample holder 30 placed in the carrying path 50. As shown in FIGS. 2 and 3, the carrying apparatus 20 has the sample holder 30, the carrying path 50, a rotary member 60, and a helical member driver 70.

As shown in FIG. 3, the sample holder (holder) 30 is configured to be able to house the sample 11. The sample holder 30 has a test tube holding portion 31, a held portion 32 which is formed at one end of the test tube holding portion 31 and which is held by a later-described traveling wall 53, a top flange 33 formed on the upper edge of the held portion 32, and a bottom flange 34 formed on the lower edge of the held portion 32.

The test tube holding portion 31 has a base 35, and arms 36 provided in the base 35. The base 35 is, for example, cylindrical. The arms 36 are fixed to the upper end of the base 35, and extend upward. The arms 36 are arranged along a circle around the central line of the base 35 at the upper end of the base 35. Each of the arms 36 is made of, for example, a metallic material, and is elastic. A catching portion 37 is formed at the upper end of each of the arms 36.

The catching portion 37 is formed by bending each the arms 36 inward. The space between the catching portions 37 of the arms 36 is narrower than the space between other parts of the arms 36. The space between the catching portions 37 of the arms 36 is provided to be thinner than the test tube 12. If the test tube 12 is inserted into the test tube holding portion 31, the test tube 12 spreads the catching portions 37. The spread arms 36 are restored inward by elasticity. The test tube 12 is caught and held by the elastic force of each of the arms 36.

The held portion 32 is provided at the lower end of the base 35, and projects downward from the base 35. When the held portion 32 is cut in a direction perpendicular to its axial line, the section of the held portion 32 has a size that fits in the lower end face of the base 35. The held portion 32 is cylindrical by way of example, and its axial line is collinear with the axial line of the base 35. Therefore, the held portion 32 has a shape which is diametrically smaller than the base 35.

The top flange 33 is provided on the upper edge of the held portion 32, and projects diametrically outward from the held portion 32. The bottom flange 34 is provided on the lower edge of the held portion 32, and projects diametrically outward from the held portion 32. A magnet (holder side member) 38 is housed at the lower end of the bottom flange 34. The magnet 38 is located in the center of the bottom flange 34.

FIG. 4 is a plan view showing one end of the carrying path 50 in a longitudinal direction. As shown in FIGS. 2, 3, and 4, the carrying path 50 has a pair of sidewalls 52, the traveling wall 53, and a bottom wall 54. The sidewalls 52 are fixed to the bottom wall 54. The sidewalls 52 vertically extend to face each other. The sidewalls 52 are located apart from each other to have a gap which can house the sample holder 30 in between.

The traveling wall 53 is provided in the center of the sidewalls 52 in a vertical direction, and extends in the width direction. More specifically, as shown in FIG. 3, the traveling wall 53 provided in one sidewall 52 projects toward the other sidewall 52. The traveling wall 53 provided in the other sidewall 52 projects toward one sidewall 52. Ends 53*a* of the traveling walls 53 are not in contact with each other, and have a space (communication groove) S1 formed in between.

The space S1 is formed to be able to house the held portion 32 of the sample holder 30. More specifically, the distance between the ends 53*a* is slightly greater than the diameter of the held portion 32. The distance between the ends 53*a* is smaller than the diameters of the top flange 33 and the bottom flange 34. Therefore, the held portion 32 can be housed between the ends 53*a*. If the held portion 32 is housed between the ends 53*a*, the top flange 33 comes into contact with the upper end face of the traveling wall 53.

Inwardly projecting projections 55 are formed at the upper ends of the sidewalls 52. A space larger than the thickness of the top flange 33 is defined between the projection 55 and the traveling wall 53.

When the sample holder 30 is mounted on the traveling wall 53, the projection 55 is located above the top flange 33 on the sample holder 30, and projects to the position where the projection 55 overlaps the top flange 33 in the vertical direction.

The projections 55 extend to the position where the projections 55 do not contact the test tube holding portion 31 when the held portion 32 is held between the ends 53*a* of the traveling wall 53. More specifically, the distance between the projections 55 is greater than the diameter of the base 35 of the test tube holding portion 31.

Therefore, when the sample holder 30 travels on the traveling wall 53, the top flange 33 does not contact the projections 55. If the sample holder 30 is pulled upward, the top flange 33 contacts the projections 55, so that the sample holder 30 is prevented from coming off the carrying path 50.

The space between the sidewalls 52 is divided into two parts in the vertical direction by the traveling wall 53. The space above the traveling wall 53 is a traveling space where the sample holder 30 travels. The space under the traveling wall 53 is a rotary member housing space. The rotary member housing space is formed so that the rotary member 60 and part of the helical member driver 70 can be housed.

Figure 5:
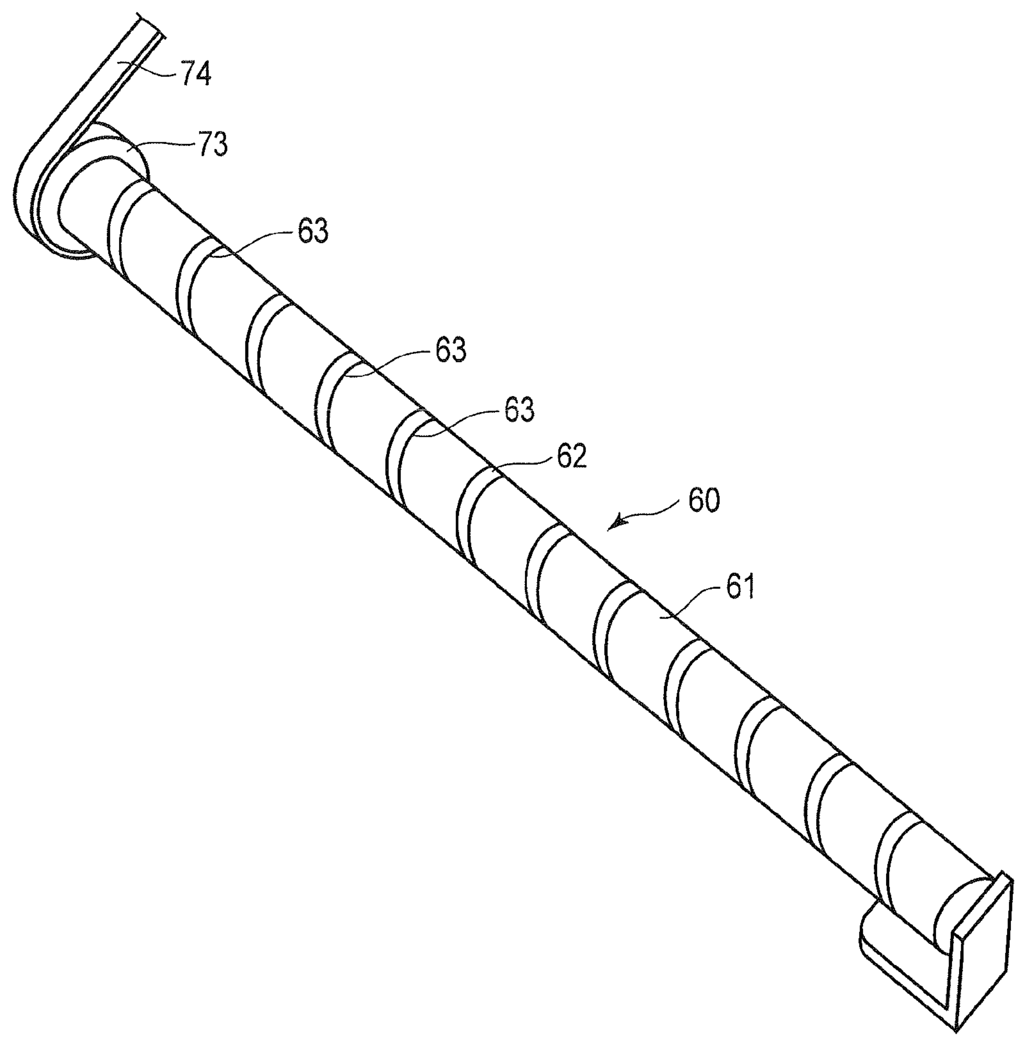
FIG. 5 is a perspective view showing a rotary member of the carrying apparatus.

FIG. 5 is a perspective view showing the rotary member 60. As shown in FIG. 5, the rotary member 60 has a cylindrical body 61, and a helical member 62 provided in the circumferential part of the body 61. The main material of the helical member 62 is iron, and the helical member 62 has such properties as to be attracted to the magnet 38 by magnetic force of the magnet 38.

The body 61 is made of, for example, a resin, and is a cylindrical member. An inwardly recessed groove 63 is formed in the circumferential surface of the body 61. The groove 63 has a helical shape around the axial line of the body 61, and extends from one end of the body 61 to the other. The helical member 62 is housed in the groove 63. The helical member 62 is fixed to the groove 63. The axial line of the helical member 62 is located on the axial line of the body 61.

The axial line of the rotary member 60 is located in the center of the width direction of the carrying path 50. The size of the body 61 in the diametrical direction and the size of the helical member 62 in the diametrical direction are such sizes that the body 61 and the helical member 62 do not contact the bottom flange 34 and the magnet 38 of the sample holder 30.

As shown in FIG. 4, the helical member driver (rotation unit) 70 has a drive electric motor 71, a first pulley 72 rotatably fixed integrally to an output shaft of the drive electric motor 71, a second pulley 73 rotatably fixed integrally to the rotary member 60, and a belt member 74 put around the pulleys 72 and 73.

The drive electric motor 71 is located in the vicinity of one end of the carrying path 50 outside the carrying path 50. The axial line of the second pulley 73 is located on the axial line of the body 61 of the rotary member 60. The second pulley 73 is out of the carrying path 50, and is adjacent to the first pulley 72. The belt member 74 is formed to be able to transmit the rotation of the first pulley 72 to the second pulley 73.

As shown in FIG. 1, the stopper apparatus 100 is formed so that the sample holder 30 can be stopped at the position where the processing apparatus 90 processes the sample 11. Specifically, the stopper apparatus 100 has a stopper 101 and a stopper driver 102. The stopper 101 is formed movably between the position where the stopper 101 can contact the sample holder 30 in the carrying path 50 and the position where the stopper 101 does not contact the sample holder 30. The stopper driver 102 is formed to be able to drive the stopper 101. The driving referred to here means to move the stopper 101 between the position where the stopper 101 can contact the sample holder 30 and the position where the stopper 101 does not contact the sample holder 30.

The controller 110 is formed to be able to control the operation of the processing apparatus 90, the operation of the drive electric motor 71, and the operation of the stopper driver 102.

Next, the operation of the sample processing system 10 is described. First, the test tube 12 is housed in the sample holder 30 placed on the carrying path 50 by, for example, an operator. The controller 110 drives the drive electric motor 71 when the test tube 12 is housed in the sample holder 30.

If the drive electric motor 71 is rotated, the first pulley 72 rotates. The rotation of the first pulley 72 is transmitted to the second pulley 73 by the belt member 74. The second pulley 73 is rotated by the belt member 74. The rotary member 60 rotates around its axial line in response to the rotation of the second pulley 73.

The helical member 62 rotates in response to the rotation of the rotary member 60. If the helical member 62 rotates around its axial line, upper ends 65 facing between the ends 53*a* in the helical member 62 appear to move along a carrying direction A, as shown in FIG. 4. Since the helical member 62 only rotates around its axial line in actuality, the upper ends 65 do not move in the carrying direction A.

When the upper ends 65 appear to move in the carrying direction, the sample holder 30 is attracted to the upper ends 65 by the magnetic force of the magnet 38. As a result, the sample holder 30 is carried along the carrying path 50.

When the sample holder 30 reaches the processing apparatus 90, the controller 110 drives the stopper driver 102 to move the stopper 101 to the position where the stopper 101 can contact the sample holder 30. When the stopper 101 is moved to the position where the stopper 101 can contact the sample holder 30, the traveling of the sample holder 30 is stopped by the contact of the sample holder 30 with the stopper 101. A sensor which detects that the sample holder 30 has reached the processing apparatus 90 may be provided in the carrying path 50. The stopper driver 102 may be driven in accordance with the detection result of the sensor.

The controller 110 controls the processing apparatus 90 to process the sample 11 in the test tube 12 housed in the sample holder 30. Even when the processing apparatus 90 is in the middle of processing, the drive electric motor 71 is driven, and the rotary member 60 continues rotating. When the processing of the sample 11 is finished, the controller 110 controls the stopper driver 102 to move the stopper 101 to the position where the stopper 101 does not contact the sample holder 30.

When the stopper 101 has moved to the position where the stopper 101 does not contact the sample holder 30, the sample holder 30 resumes traveling by the attraction of the magnet 38 to the upper ends 65 of the helical member 62.

In the sample processing apparatus having such a configuration, the sample holder 30 and the rotary member 60 do not contact each other. Therefore, the rotary member 60 is prevented from being worn.

The helical member 62 is made of a metallic material containing iron as the main material that costs less and is easier to process than the magnet. Consequently, the carrying apparatus 20 can be relatively easily produced.

The upper ends 65 of the helical member 62 face the magnet 38 through the space between the ends 53*a* of the traveling wall 53, so that the magnetic force of the magnet 38 can be efficiently used.

In the present embodiment, the helical member 62 is formed by iron as the main material between the sample holder 30 and the helical member 62 of the rotary member 60 as an example of means for attracting the sample holder 3C and the helical member 62 to each other, and the magnet 38 is provided in the sample holder 30.

Thus, the magnet 38, and the metal which is attracted to the magnet are used. As another example, the helical member 62 may be formed by a magnet as the main material, and a material such as a metallic material that is attracted to the helical member 62 may be provided in the sample holder 30.

Alternatively, the helical member 62 may be made of a magnet, and a magnet which is attracted to the helical member 62 may be provided in the sample holder 30. Alternatively, the helical member 62 may be made of a magnet. Thus, the helical member 62 may be entirely made of a magnet, or may be partly provided with a magnet.

In short, the helical member 62 has only to be made of one of the materials having such properties as to be attracted to each other or partly provided with one of the materials, and the other has only to be provided in the sample holder 30 so that the sample holder 30 moves in response to the movement of the helical member 62.

Alternatively, one of two materials having such properties as to repel each other may be provided in the sample holder 30, and the helical member 62 may be made of the other or partly provided with the other. One example of this structure is a pair of magnets that repel each other. According to this structure, if the upper ends 65 of the helical member 62 apparently move, the sample holder 30 moves due to repulsion working between the magnets.

Although one rotary member 60 is used in the present embodiment, the present invention is not limited to this. For example, multiple rotary members 60 may be arranged along the carrying path 50. Moreover, in the present embodiment, the controller 110 of the sample processing system 10 controls the operation of the carrying apparatus 20 by way of example. That is, the controller 110 functions as a controller which controls the operation of the carrying apparatus 20. As another example, an exclusive controller which controls the operation of the carrying apparatus 20 may be provided.

This invention is not to be merely limited to the embodiments described above, and modifications of components can be made at the stage of carrying out the invention without departing from the spirit thereof. Furthermore, various inventions can be made by properly combining the components disclosed in the embodiments described above. For example, some of all the components shown in the embodiments described above may be eliminated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A carrying apparatus comprising:

a holder including an object-to-be-carried holding portion which holds an object to be carried, a top flange provided at a lower edge of the object-to-be-carried holding portion, a held portion provided at a lower edge of the top flange, and a bottom flange provided at a lower edge of the held portion;

a holder side member provided at a lower edge of the holder;

a carrying path including a pair of side walls and a traveling wall which is provided between the pair of side walls and on which the holder travels, the traveling wall including a communication groove formed in a central part of the traveling wall in a width direction;

a helical member disposed along the carrying path opposite to the object-to-be-carried holding member across the traveling wall, the helical member being configured to generate, between the holder side member and the helical member, a first force in a direction to depart from the holder side member or a second force to attract the holder side member, and being configured to move the holder along the traveling wall by the first force or the second force by rotation; and a rotation unit configured to rotate the helical member.

* * * * *